United States Patent

(12) United States Patent
Xu et al.

(10) Patent No.: US 7,884,220 B2
(45) Date of Patent: Feb. 8, 2011

(54) PROCESS FOR PURIFYING PPPBP

(75) Inventors: Zhongqi Xu, Shanghai (CN); Guohua Xiu, Shanghai (CN); Tong Sun, Shanghai (CN); Jingwu Yang, Shanghai (CN)

(73) Assignee: General Electric Company, Schenectady, NY (US)

( * ) Notice: Subject to any disclaimer, the term of this patent is extended or adjusted under 35 U.S.C. 154(b) by 811 days.

(21) Appl. No.: 11/687,943

(22) Filed: Mar. 19, 2007

(65) Prior Publication Data

US 2008/0234496 A1 Sep. 25, 2008

(51) Int. Cl.
C07D 209/44 (2006.01)

(52) U.S. Cl. ...................................... 548/472
(58) Field of Classification Search ........................ None
See application file for complete search history.

(56) References Cited

U.S. PATENT DOCUMENTS

| 5,310,593 | A | * | 5/1994 | Tsujimoto et al. ........... 428/166 |
|---|---|---|---|---|
| 5,344,910 | A | | 9/1994 | Sybert |
| 5,980,612 | A | * | 11/1999 | Kelly ........................... 95/106 |
| 6,423,657 | B1 | * | 7/2002 | Wang et al. ................... 502/25 |
| 7,135,577 | B2 | | 11/2006 | Rai et al. |
| 7,563,817 | B2 | * | 7/2009 | Ganesan et al. ............. 514/415 |
| 2005/0222334 | A1 | | 10/2005 | Srinivasan et al. |
| 2005/0228137 | A1 | * | 10/2005 | Srinivasan et al. .......... 525/186 |
| 2005/0288517 | A1 | * | 12/2005 | Rai et al. .................... 548/472 |
| 2007/0010619 | A1 | * | 1/2007 | Chatterjee et al. ............. 525/67 |
| 2008/0033123 | A1 | * | 2/2008 | Srinivasan et al. ............. 526/64 |
| 2008/0058497 | A1 | * | 3/2008 | Ganesan et al. ............. 528/367 |
| 2008/0242873 | A1 | * | 10/2008 | Basale et al. ................. 548/472 |
| 2008/0286193 | A1 | * | 11/2008 | Bento et al. ................. 423/461 |

FOREIGN PATENT DOCUMENTS

| EP | 1582549 A1 | 10/2005 |
|---|---|---|
| FR | 1519027 A | 3/1968 |
| JP | 60-211000 | * 10/1985 |
| WO | 2007070528 A1 | 6/2007 |

OTHER PUBLICATIONS

Bajaj et al., "PAN-based Activated Carbon Fibers: Production, Characterization and Applications", Chemical Abstracts, 128:168596, 1998.*
Tanaka, Eiji, "Decolorization of Sugar Syrups", Chemical Abstracts, 104:90871, 1986.*
Yang, Chin-Ping and Lin, Jiun-Hung, "Syntheses and Properties of Aromatic Polyamides and Polyimides Based on N-Phenyl-3,3-Bis[4-(p-aminophenoxy)phenyl]phthalimidine", Journal of Polymer Science, Part A: Polymer Chemistry Edition 32 (Jan. 30, 1994), No. 2, New York, US, John Wiley & Sons, Inc. (pp. 369-382).
International Search Report for PCT/US2007/072840 International Filing Date May 7, 2007, Mailing Date Feb. 18, 2008 (6 pages).
Written Opinion of the International Searching Authority for PCT/US2007/072840 International Filing Date May 7, 2007, Mailing Date Feb. 18, 2008 (7 pages).

* cited by examiner

*Primary Examiner*—Fiona T Powers
(74) *Attorney, Agent, or Firm*—Fay Sharpe LLP; Richard M. Klein

(57) ABSTRACT

A method for decoloring 2-phenyl-3,3-bis(4-hydroxyphenyl) phthalimidine ("p,p-PPPBP") is disclosed. The method comprises contacting a liquid solution containing p,p-PPPBP and the common impurities o,p-PPPBP and aminophenone with activated carbon fibers. The activated carbon fibers adsorb the impurities, resulting in a purified solution of p,p-PPPBP. The activated carbon fibers can then be regenerated, such as with a methanol solution having a highly basic pH.

22 Claims, 2 Drawing Sheets

PROCESS FOR PURIFYING PPPBP

BACKGROUND

This disclosure relates, in various embodiments, to processes for purifying 2-phenyl-3,3-bis(4-hydroxyphenyl)phthalimidine.

Phenolphthalein has been used as an aromatic dihydroxy compound to synthesize monomers for preparing polycarbonates, which are generally characterized with excellent clarity, excellent ductility, and high glass transition temperatures. Certain derivatives of phenolphthalein have also been used as aromatic dihydroxy compounds to synthesize monomers to prepare polycarbonate resins as well as polyarylate resins. In particular, 2-phenyl-3,3-bis(hydroxyphenyl)phthalimidine ("PPPBP") is useful as a monomer for polycarbonate resins.

para,para-PPPBP ("p,p-PPPBP") can be synthesized by refluxing phenolphthalein and aniline hydrochloride in aniline for 6 hours, followed by recrystallization from ethanol. p,p-PPPBP has the chemical structure of Formula (I):

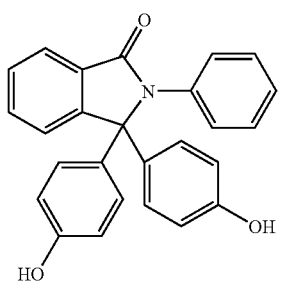

Formula (I)

As is evident, the "p,p-" designation is used because both hydroxyls are in the p-position. During this synthesis, undesired side products and impurities are created. Two such undesired byproducts are ortho,para-PPPBP ("o,p-PPPBP") and aminophenone. o,p-PPPBP has the chemical structure of Formula (II) and aminophenone has the chemical structure of Formula (III):

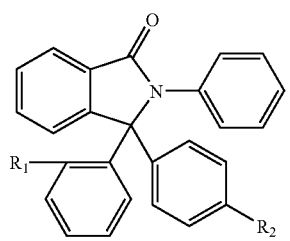

Formula (II)

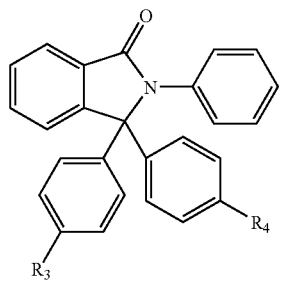

Formula (III)

wherein $R_1$, $R_2$, $R_3$, and $R_4$ are independently —OH or —$NH_2$; and at least one of $R_3$ and $R_4$ is —$NH_2$. These byproducts arise as a result of the synthesis method described above. Although the structures of Formulas (II) and (II) encompass several different compounds, they will be treated as one for the purposes of this disclosure.

Other impurities include residual levels of phenolphthalein and other phenolphthalein by-products. Impurities affect polymer properties considerably. They can hinder polymerization and result in low weight average molecular weight polycarbonates of, for example, less than about 22,000 Daltons for melt polymerization and less than about 50,000 Daltons for an interfacial polymerization that exhibit undesirable physical properties, such as increased brittleness, that is, poor ductility properties. Furthermore, they affect the transparency of the polymer product by producing discoloration. A major objective of such polycarbonates is transparency.

Because impurities affect the final polymer product, p,p-PPPBP must be purified after synthesis. The purification process, also known as the decoloring process, reduces and/or removes these impurities from the intermediate polymer mixture to obtain the final desired product. Monomer-grade p,p-PPPBP should contain impurities at a level of less than 15 parts per million (ppm).

In present decoloring processes, the intermediate polymer mixture, containing a mixture of p,p-PPPBP, phenolphthalein, o,p-PPPBP, aminophenone, and other byproducts, is dissolved in an aqueous inorganic base. This solution is then treated with an adsorbent, usually powder activated carbon ("PAC"), to remove the impurities. After treatment with PAC, the resulting mixture is then filtered to obtain the purified p,p-PPPBP in aqueous solution. This process is repeated several times to achieve the desired purity level.

This process has several disadvantages. First, the PAC usually absorbs between 7-8% of the desired p,p-PPPBP product. Because PAC is difficult to regenerate, it is usually discarded after one use and the absorbed product is consequently lost. In addition, the cost of the PAC, which is discarded, is relatively high due to the need for a specific grade of PAC. Finally, because the PAC is of small diameter (to increase surface area for reaction), it is difficult to filter the PAC out of the mixture to obtain the p,p-PPPBP in aqueous solution.

There is a continuing need for the removal and/or reduction of impurities from p,p-PPPBP. Such a purification process should also be cost-effective and feasible on a large scale.

REFERENCES

U.S. patent application Ser. No. 10/815,880, to Srinivasan et al, filed Mar. 31, 2004 and published as U.S. Patent Application Publication No. 2005/0222334, discloses methods for producing and purifying 2-phenyl-3,3-bis(4-hydroxyphenyl)phthalimidine monomers.

U.S. patent application Ser. No. 11/263,132, to Chatterjee et al, filed Oct. 31, 2005 and published as U.S. Patent Application Publication No. 2007/0010619, discloses polycarbonate resins containing 2-phenyl-3,3-bis(4-hydroxyphenyl)phthalimidine monomers.

U.S. patent application Ser. No. 11/300,225, to Ganesan et al., filed Dec. 14, 2005, discloses a method for purifying a 2-aryl-3,3-bis(hydroxyaryl)phthalimidine compound by contacting it with an acidic material, an organic acid chloride, an organic anhydride, or a combination thereof.

U.S. Pat. No. 5,344,910, to Sybert, issued Sep. 6, 1994, discloses heat-resistant polycarbonate resins containing 2-alkyl-3,3-bis(p-hydroxyphenyl) phthalimidine.

U.S. Pat. No. 7,135,577, to Rai et al, issued Nov. 14, 2006, also discloses methods for producing and purifying 2-phenyl-3,3-bis(4-hydroxyphenyl)phthalimidine monomers.

Each reference listed above is hereby incorporated by reference in its entirety.

SUMMARY

An adsorption process for purifying or decoloring p,p-PPPBP is disclosed in various embodiments. A reaction synthesizing p,p-PPPBP creates an intermediate mixture comprising p,p-PPPBP and byproducts such as o,p-PPPBP and aminophenone. The intermediate mixture may also comprise other byproducts. A crude product is precipitated from the intermediate mixture which comprises the p,p-PPPBP and byproducts. The crude product is dissolved in an aqueous base to form a pre-purification solution. The pre-purification solution is then contacted with adsorbent activated carbon fibers ("ACF") to filter the o,p-PPPBP and/or aminophenone out of the solution and decolor the solution. In particular embodiments, the activated carbon fibers are in the form of a sheet which is rolled and packed into a cylinder. In other embodiments, the activated carbon fibers are cut into chip form and then packed into a cylinder.

After filtering the pre-purification solution through the activated carbon fibers, a purified or decolored solution comprising p,p-PPPBP is obtained. The decolored solution contains lower levels of o,p-PPPBP and/or aminophenone than the pre-purification solution. In specific embodiments, the decolored solution contains less than 15 ppm of the impurities.

In further embodiments, the contacting occurs at elevated temperatures from about 20° C. to about 90° C. In more specific embodiments, the contacting occurs at an elevated temperature of from about 60° C. to about 80° C. In more specific embodiments, the contacting occurs at about 70° C.

The pre-purification solution may be contacted with the activated carbon fibers at a rate of from about 6 to about 10 milliliters per minute. The contacting may occur for a period of from about 1 to about 4 hours.

After the pre-purification solution has been filtered through the activated carbon fibers, the activated carbon fibers are regenerated. In some embodiments, the regeneration is accomplished by extracting the activated carbon fibers with an organic solvent. The activated carbon fibers may be extracted multiple times. In other specific embodiments, the organic solvent is methanol and in further embodiments, the organic solution has a basic pH. In embodiments, the pH of the organic solvent or solution used to regenerate the activated carbon fibers is from about 12 to about 14. The regeneration may also occur at about 70° C.

The activated carbon fibers can be prepared by water rinsing, steaming, or vacuum suction. They may be prepared for a period of from about 10 to about 30 minutes.

The decoloring process may be done in a continuous or a batch manner.

These and other non-limiting features or characteristics of the present disclosure will be further described below.

BRIEF DESCRIPTION OF THE DRAWINGS

The following is a brief description of the drawings which are provided for the purposes of illustrating one or more of the exemplary embodiments described herein and not for the purposes of limiting the same.

DETAILED DESCRIPTION

Figure 1:
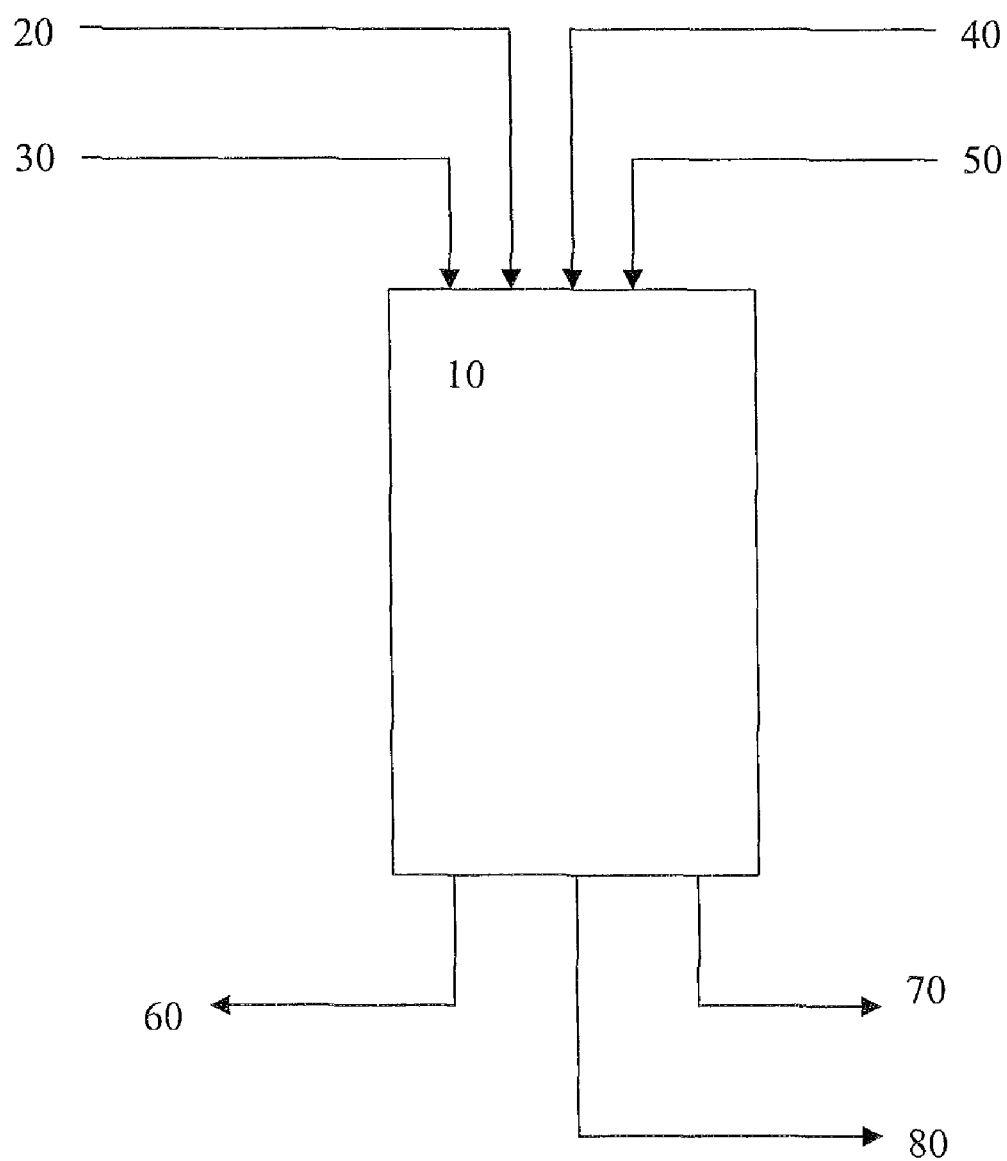
FIG. 1 is a schematic diagram of an apparatus which may be used to practice the decoloring process of the present disclosure.

The exemplary embodiments of this disclosure are more particularly described below with reference to the drawings. Although specific terms are used in the following description for clarity, these terms are intended to refer only to the particular structure of the various embodiments selected for illustration in the drawings and not to define or limit the scope of the disclosure. The same reference numerals are used to identify the same structure in different Figures unless specified otherwise. The structures in the Figures are not drawn according to their relative proportions and the drawings should not be interpreted as limiting the disclosure in size, relative size, or location.

2-phenyl-3,3-bis(hydroxyphenyl)phthalimidine ("PP-PBP") can be synthesized from a reaction of phenolphthalein and an aniline salt. The reaction usually takes place in an acid solution, which facilitates formation of the PPPBP product. Examples of suitable acids include hydrochloric acid, sulfuric acid, and nitric acid. An acid catalyst is also usually included in the reaction mixture, such as aniline hydrochloride. In particular embodiments, the aniline hydrochloride serves as both the aniline salt and the acid catalyst. The reaction of phenolphthalein with aniline proceeds by a condensation reaction to form the desired p,p-PPPBP product. An excess of aniline may be used to keep the reaction proceeding in the forward direction. Similarly, a higher reaction temperature with or without removal of water byproduct also facilitates product formation. However, controlling the temperature of the reaction mixture along with controlling the rate of water removal enhances the selectivity of the reaction and suppresses formation of the undesired o,p-PPPBP and/or aminophenone byproduct. When controlled properly, a reaction mixture comprising phenolphthalein, aniline (as solvent), and aniline hydrochloride (as catalyst) can be reacted to obtain an intermediate mixture comprising about 97-98 percent p,p-PPPBP and about 2-3 percent of undesired byproduct.

The intermediate mixture is then quenched with an aqueous acid to precipitate the p,p-PPPBP and the byproducts, which form a crude product. The crude product is then dissolved in an aqueous base, such as sodium hydroxide, to make a pre-purification solution.

The pre-purification solution is then contacted with adsorbent activated carbon fibers ("ACF") to filter impurities out of the solution, decoloring it. Previously, activated carbon was used in the form of powder activated carbon ("PAC") and/or granular activated carbon ("GAC"). PAC and GAC have several disadvantages. As previously mentioned, they tend to absorb the desired product, which is lost. They are also difficult to filter in order to obtain the desired product. In addition, their reaction kinetics are relatively slow. Using ACF, on the other hand, increases the yield of p,p-PPPBP which is recovered. ACF are more easily regenerated and can be used scores of times. Because ACF are in a fibrous form, they are easier to handle and do not require secondary operations like filtration to recover p,p-PPPBP. ACF also have higher adsorption capacity and higher mass transfer rates for both adsorption and desorption because of their thin-fiber shape.

The activated carbon fibers are packed into a column for ease of use. Activated carbon fibers may be formed from cellulose and acrylic precursors. Activated carbon fibers are usually provided in the form of a sheet. This sheet may be rolled up and packed into the column. Alternately, the sheet may be cut into chips and then packed into the column. The chips may have any shape; in one embodiment, the chips are cut into circles and then stacked on top of each other into the column. In another embodiment, two types of circular chips having two diameters are alternately stacked into the column. These forms allow the column to be packed with near 100% efficiency.

It has been found that the decoloring process using activated carbon fibers is more efficient when performed at an elevated temperature. In some embodiments, the contacting is performed at a temperature of from about 20° C. to about 90° C. In specific embodiments, the contacting is performed at a temperature of from about 60° C. to about 80° C. In more specific embodiments, the contacting is performed at a temperature of about 70° C. The elevated temperature can be obtained by either heating the pre-purification solution or by heating the column itself. However, these temperature ranges are stated in terms of the temperature of the solution. It may be necessary to heat the column to a higher temperature in order to obtain these temperatures in the solution.

The pre-purification solution should flow through the adsorption column at as low a rate as possible to increase the residence time of the solution in the ACF. In embodiments, the flow rate is from about 6 to about 10 milliliters per minute (ml/min). Of course, this flow rate may change depending on the amount of ACF used, the operating temperature, and mass transfer hindrance. For example, an adsorption column with a larger diameter and/or length can accommodate a higher flow rate.

After filtering the pre-purification solution through the packed activated carbon fibers, a purified or decolored solution comprising p,p-PPPBP is obtained. As used herein, the terms "purified" and "decolored", when referring to the p,p-PPPBP obtained, are used interchangeably. The decolored solution contains lower levels of o,p-PPPBP and/or aminophenone than the pre-purification solution. The decolored solution is then quenched again with an aqueous acid to precipitate the purified p,p-PPPBP. The precipitate may then be stirred with an aliphatic alcohol to remove any remaining trace of phenolphthalein, then filtered to obtain a cake of purified p,p-PPPBP. Suitable alcohols include methanol, ethanol, butanol, isopropanol, and the like. In particular, the level of o,p-PPPBP and/or aminophenone impurities is reduced to ppm levels, so that the purified p,p-PPPBP contains less than 15 ppm of o,p-PPPBP and/or aminophenone.

If the cake of p,p-PPPBP is not pure enough, the decoloring process can be repeated by dissolving the cake of p,p-PPPBP with an aqueous base and filtering it through activated carbon fibers again. Alternatively, the decolored solution is not quenched to precipitate purified p,p-PPPBP, but is used as the input to another adsorption column.

After the pre-purification solution has been decolored by the activated carbon fibers, the activated carbon fibers contain impurities such as phenolphthalein, o,p-PPPBP, and/or aminophenone, along with residual levels of the desired p,p-PPPBP product. One benefit of using activated carbon fibers instead of PAC or GAC is that the fibers can be easily regenerated, whereas PAC and GAC cannot. PAC and GAC end up being used only once before they must be replaced. PAC and GAC are commercially available as NORIT from Norit Corporation. Activated carbon fibers, on the other hand, can be easily regenerated and can be used scores of times before being replaced.

The activated carbon fibers can be regenerated in several different ways. They can be regenerated by exposure to a basic solution. For example, a regeneration solution may be an aqueous solution of NaOH which is run through the column to regenerate the activated carbon fibers. They can also be regenerated by extraction, for example with methanol. In specific embodiments, they are regenerated with a basic methanol solution having a pH of from about 12 to about 14. They can also be regenerated by exposure to an acidic solution. Finally, the ACF can be heated to release adsorbed components. In some embodiments, the regeneration step comprises multiple purging steps using one or more of these methods. In particular embodiments, the regeneration includes from about 2 to about 5 steps.

The decoloring process of the present disclosure can be performed in a continuous or batch manner. Using the process, p,p-PPPBP can be purified by the reduction and/or removal of the o,p-PPPBP and/or aminophenone impurities. Variations of this process can achieve this result. For example, the length of the adsorption column can be increased or the concentration of p,p-PPPBP and/or byproducts can be reduced in the solution fed into the column to increase the yield.

In preparing the column containing the activated carbon fibers for adsorption, the column may be washed. For example, fresh water can be run through the column or the column may be exposed to vacuum. This preparation step can last for from about 10 to about 30 minutes. The pre-purification solution can have a residence time of from about 1 hour to about 4 hours. In a specific embodiment, the solution is run for about 2 hours. The regeneration step can last for from about 2 to about 10 hours. Generally, the adsorption step, where the pre-purification solution is run through the column, takes the most time and runs for longer than both the preparation step and the regeneration step combined.

FIG. 1 is a schematic diagram of an apparatus which may be used to practice the purification process of the present disclosure. The adsorption column 10 contains the activated carbon fibers used in the process. If a preparation step is used, vacuum suction 70 may be used to prepare the column. During the decoloring step, the pre-purification solution 20 enters the column and purified solution 60 exits the column. After the purifying step is completed, the column is regenerated. In one embodiment, the activated carbon fibers are regenerated by purging the column 10 first with nitrogen gas 40, then with a regeneration solution 30, then with steam at an elevated pressure 50. The regeneration solution 30, after going through the column 10, is recovered as waste solution 80.

Figure 2:
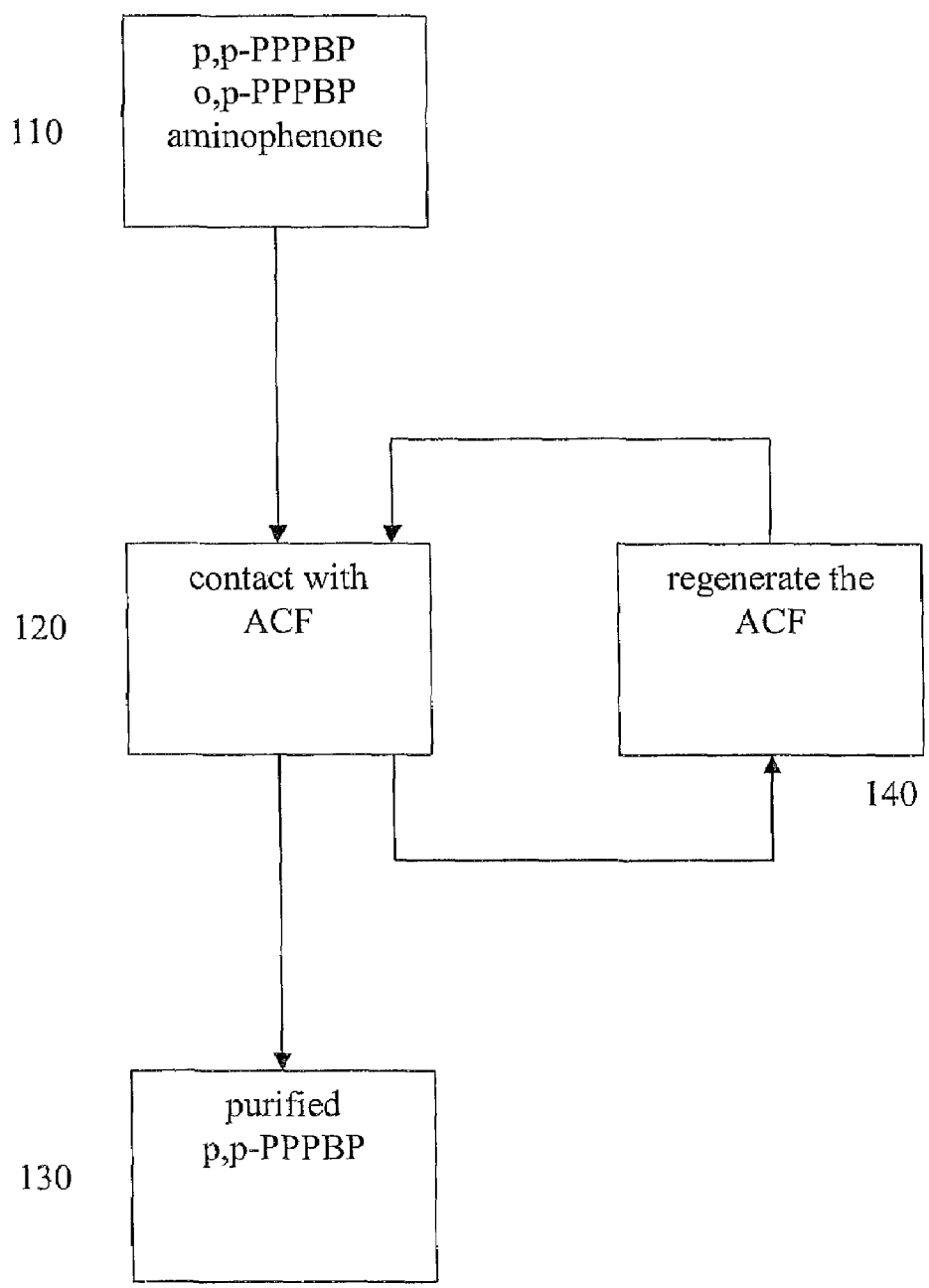
FIG. 2 is a schematic showing the steps of the decoloring process of the present disclosure.

FIG. 2 is a schematic showing the process steps of the present disclosure. A pre-purifying solution is provided comprising p,p-PPPBP and impurities such as o,p-PPPBP and/or aminophenone 110. The pre-purifying solution is contacted with the activated carbon fibers 120. A decolored solution comprising p,p-PPPBP is obtained 130. The activated carbon fibers are regenerated 140.

The present disclosure is further illustrated in the following non-limiting working examples, it being understood that these examples are intended to be illustrative only and that the disclosure is not intended to be limited to the materials, conditions, process parameters and the like recited herein. All proportions are by weight unless otherwise indicated.

EXAMPLES

Preparation of Pre-Purification Solution

About 500 grams of wet cake comprising p,p-PPPBP and aminophenone was mixed with 8 liters of water and 142 grams of NaOH. This solution was then filtered to remove insoluble particles to form the pre-purification solution. The wet cake contained >95% p,p-PPPBP and about 1.5% impurities such as o,p-PPPBP and aminophenone.

Pre-Treatment of Activated Carbon Fibers

The activated carbon fibers (ACF) were washed with distilled water, then dried in an oven at 100° C. This pretreatment maximized the initial capacity of the ACF.

Determination of Purity of p,p-PPPBP by HPLC

HPLC was used to determine the purity of p,p-PPPBP in the following Examples. Trace amounts of the reactants (phenolphthalein) and byproducts (o,p-PPPBP and/or aminophenone) were expected to be present in the final product. However, other unknown impurities could also be expected. Phenolphthalein was determined using an external calibration standard method and other impurities were determined using the response factor of PPPBP. The HPLC equipment used the following conditions:

| | |
|---|---|
| Instrument: | Shimadzu LC-10 Advp |
| Column: | ZORBAX Eclipse XDB-Phenyl, 250 * 4.6 mm, 5.0-micron. |
| Mobile phase: | 0.02% v/v $H_3PO_4$ in deionized water, Acetonitrile |
| Column temperature: | 40° C. |
| Flow rate: | 1.0 ml/min |
| Detector wavelength: | 230 nm PDA |
| Data acquisition: | 30 min |
| Injection volume: | 10 μl |

Example 1

Activated carbon fibers obtained from two different vendors, Anshan & Sutong, were pretreated as described above. Four flasks were prepared; each flask contained about 2.0 grams of ACF. Two flasks contained ACF from Anshan and two flasks contained ACF from Sutong.

200.0 mL of the pre-purification solution was placed into each flask. The flasks were then shaken for two hours. Two flasks, one from each vendor, were shaken at 20° C. and the other two flasks were shaken at 70° C. The solution was then analyzed by HPLC to measure the concentration change of the aminophenone. The initial peak area for aminophenone was 175,537. Results are shown in Table 1.

TABLE 1

| Sample | Vendor | Temperature | Post-Purification Peak Area | Removal Ratio (%) |
|---|---|---|---|---|
| 1 | Anshan | 20° C. | 170,989 | 2.59 |
| 2 | Anshan | 70° C. | 169,914 | 3.20 |
| 3 | Sutong | 20° C. | 147,772 | 15.82 |
| 4 | Sutong | 70° C. | 30,756 | 82.48 |

The data showed that the adsorption temperature significantly affected the removal ratio of the aminophenone impurity in the Sutong material. In particular, the concentration of aminophenone in Sample 4 was reduced from 84.5 ppm to 12.4 ppm upon ACF treatment.

Because the difference in performance of the ACF from the two vendors was significant, the ACF themselves were examined. Table 2 lists of properties of the ACF from the two vendors.

TABLE 2

| Property | Anshan ACF | Sutong ACF |
|---|---|---|
| BJH Adsorption cumulative surface area of pores having a radius between 8.5 Å and 1500 Å ($m^2/g$) | 107.666 | 289.837 |
| BJH Adsorption cumulative volume of pores having a radius between 8.5 Å and 1500 Å ($cm^3/g$) | 0.085 | 0.182 |
| Average pore width (Å) | 19.438 | 18.895 |

Pores having a radius between 8.5 Å and 1500 Å would play the most important role for purifying aminophenone because this range of pore size matches the molecular size of impurities very well. The data showed that the Sutong ACF had surface area and pore volume more than double that of the Anshan ACF. In other words, the Sutong ACF was more than twice as effective at removing impurities for the same amount of ACF.

Example 2

Activated carbon fibers from Sutong were pretreated as described above. Three flasks were prepared; each flask contained 2.0 grams of ACF. 200.0 mL of the pre-purification solution was placed into each flask. The flasks were then shaken for one, two, and three hours, respectively. Each solution was then analyzed by HPLC to measure the concentration change of the aminophenone. The initial peak area for aminophenone was 32,770. Results are shown in Table 3.

TABLE 3

| Sample | Shaking Time (hr) | Post-Purification Peak Area | Removal Ratio (%) |
|---|---|---|---|
| 1 | 1 | 7,225 | 77.95 |
| 2 | 2 | 4,196 | 87.20 |
| 3 | 3 | 4,670 | 85.75 |

Because ACF has a high adsorption speed, additional exposure does not increase the removal ratio. In the static adsorption situation shown here, an exposure time of two hours was sufficient to remove most of the aminophenone impurity.

Example 3

Activated carbon fibers from Sutong were pretreated as described above. One flask was prepared and contained 2.0 grams of ACF. 200.0 mL of the pre-purification solution was placed into the flask, then shaken for two hours at 70° C. The solution was then analyzed by HPLC to measure the concentration change of p,p-PPPBP, aminophenone, and phenolphthalein (PP). Results are shown in Table 4.

TABLE 4

| Component | Pre-Purification Peak Area | Post-Purification Peak Area | Removal Ratio (%) |
|---|---|---|---|
| p,p-PPPBP | 18,655,143 | 17,540,532 | 5.97 |
| aminophenone | 33,182 | 4,877 | 85.30 |
| PP | 371,490 | 273,557 | 26.36 |

The data showed that ACF had excellent selective adsorption of aminophenone, compared to p,p-PPPBP and PP. The removal ratio of p,p-PPPBP for ACF is also less than that of PAC (7-8%), so less desired product is lost in the purification process.

Example 4

The efficiency of various regeneration methods was tested. The following four methods were tested:

Method C: Regeneration with basic solution. 35.5 g NaOH was dissolved in 1 L of water to form a basic solution. Used ACF was put in 200 ml of the basic solution and shaken for 20 minutes at room temperature. The ACF was then removed from the basic solution and the preceding step was repeated three times. The ACF was then washed with water and dried in an oven at 100° C.

Method D: Regeneration with acidic solution. 200 ml hydrochloride acid (~12 M, 36-38 weight percent HCl) was added to 800 ml water to form an acidic solution. Used ACF was put in 200 ml of the acidic solution and shaken for 20 minutes at room temperature. The ACF was then removed from the acidic solution and the preceding step was repeated three times. The ACF was then washed with water and dried in an oven at 100° C.

Method E: Regeneration with methanol extraction. Used ACF was put in 200 ml of methanol and extracted for 70 minutes at 70° C. The ACF was then removed from the methanol and the preceding step was repeated three times. The ACF was then washed with water and dried in an oven at 100° C.

Method F: Regeneration with basic methanol solution extraction. 17.75 g NaOH was dissolved in 1 L of methanol to form a basic methanol solution. Used ACF was put in 200 ml of the basic methanol solution and extracted for 70 minutes at 70° C. The ACF was then removed from the basic methanol solution and the preceding step was repeated three times. The ACF was then washed with water and dried in an oven at 100° C.

The methods were tested by using ACF to purify a solution, then regenerating the ACF and using it anew to purify a new solution. The removal ratio for aminophenone could be calculated each time the ACF was used, indicating the regeneration effect of the regeneration method. Results are shown in Table 5.

TABLE 5

| | Aminophenone Removal Ratio after nth Regeneration (%) | | | | | |
|---|---|---|---|---|---|---|
| Regeneration Method | Initial | 1st | 2nd | 3rd | 4th | 5th |
| C | 87.4 | 3.9 | — | — | — | — |
| D | 87.4 | 3.8 | — | — | — | — |
| E | 87.4 | 40.7 | 23.8 | 21.1 | 13.5 | 10.5 |
| F | 87.4 | 78.04 | 54.22 | 37.76 | 23.1 | 14.8 |

The most effective method of regenerating the ACF was by methanol extraction, especially basic methanol extraction. However, any organic solvent should be equally effective. Basic conditions should improve the solubility of p,p-PPPBP, allowing it to be extracted into the methanol as well.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A decoloring process, comprising:
    providing a pre-purification solution comprising 2-phenyl-3,3-bis(p-phenol)phthalimidine ("p,p-PPPBP") and an impurity;
    contacting the pre-purification solution with activated carbon fibers at an elevated temperature of from about 60° C. to about 80° C. to adsorb the impurity and obtain a decolored solution comprising p,p-PPPBP and a lower concentration of impurity compared to the pre-purification solution; and
    regenerating the activated carbon fibers by desorbing the impurity wherein regenerating is accomplished by extracting the activated carbon fibers with an organic solvent.

2. The process of claim 1, wherein the activated carbon fibers are in the shape of a rolled cylindrical sheet or in the shape of cut circles stacked into a column.

3. The process of claim 1, wherein the impurity has the chemical structure of Formula (II) or Formula (III):

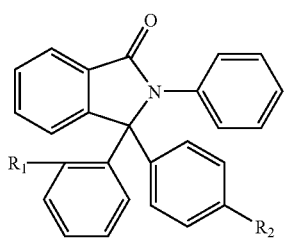

Formula (II)

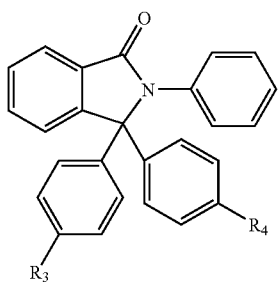

Formula (III)

wherein $R_1$, $R_2$, $R_3$, and $R_4$ are independently —OH or —NH$_2$; and at least one of $R_3$ and $R_4$ is —NH$_2$.

4. The process of claim 1, wherein the impurity is 2-phenyl-3-(o-phenol)-3-(p-phenol)phthalimidine ("o,p-PPPBP").

5. The process of claim 1, wherein the impurity is an aminophenone.

6. The process of claim 1, wherein the decolored solution contains less than 15 ppm of the impurity.

7. The process of claim 1, wherein the contacting occurs at an elevated temperature of about 70° C.

8. The process of claim 1, wherein the pre-purification solution is contacted with the activated carbon fibers at a rate of from about 6 to about 10 milliliters per minute.

9. The process of claim 1, wherein the contacting occurs for a period of from about 1 to about 4 hours.

10. The process of claim 1, wherein the organic solvent has a basic pH of from about 12 to about 14.

11. The process of claim 1, wherein the organic solvent is methanol.

12. The process of claim 1, wherein regenerating is accomplished by extracting the activated carbon fibers from about 2 to about 5 times.

13. The process of claim 1, wherein the regenerating is performed at a temperature of about 70° C.

14. The process of claim 1, further comprising: preparing the activated carbon fibers by washing them with water or by exposing them to vacuum.

15. The process of claim 14, wherein the preparing occurs for a period of from about 10 to about 30 minutes.

16. The process of claim 1, further comprising:
reacting phenolphthalein and aniline to obtain an intermediate mixture;
quenching the intermediate mixture with an aqueous acid to form a crude product; and
dissolving the crude product in an aqueous base to obtain the pre-purification solution.

17. A decoloring process, comprising:
providing a pre-purification solution comprising 2-phenyl-3,3-bis(p-phenol)phthalimidine ("p,p-PPPBP") and an impurity, the pre-purification solution having an elevated temperature of from about 60° C. to about 80° C.;
preparing activated carbon fibers by exposing them to vacuum;
decoloring the pre-purification solution using activated carbon fibers to obtain a decolored solution comprising p,p-PPPBP and having a lower concentration of the impurity than the pre-purification solution; and
regenerating the activated carbon fibers by extracting them with a basic methanol solution.

18. The process of claim 17, wherein the decoloring occurs at an elevated temperature of about 70° C.

19. The process of claim 17, wherein the decolored solution contains less than 15 ppm of the impurity.

20. The process of claim 17, wherein the basic methanol solution has a pH of from about 12 to about 14.

21. A decoloring process, comprising:
providing a pre-purification solution comprising 2-phenyl-3,3-bis(p-phenol)phthalimidine ("p,p-PPPBP") and an impurity;
contacting the pre-purification solution with clean activated carbon fibers at a temperature of from about 60° C. to about 80° C. to adsorb the impurity and obtain (1) a decolored solution comprising p,p-PPPBP and less than 15 ppm of impurity; and (2) contacted activated carbon fibers; and
regenerating the contacted activated carbon fibers by extracting the contacted activated carbon fibers with a methanol solution having a basic pH.

22. The process of claim 21, wherein the methanol solution has a pH of from about 12 to about 14.

* * * * *

UNITED STATES PATENT AND TRADEMARK OFFICE
CERTIFICATE OF CORRECTION

| | | |
|---|---|---|
| PATENT NO. | : 7,884,220 B2 | Page 1 of 1 |
| APPLICATION NO. | : 11/687943 | |
| DATED | : February 8, 2011 | |
| INVENTOR(S) | : Zhongqi Xu et al. | |

It is certified that error appears in the above-identified patent and that said Letters Patent is hereby corrected as shown below:

Title Page, Item [73] Assignee should read:

SABIC Innovative Plastics IP B.V.
PLASTICSLAAN 1
4612 PX
BERGEN OP ZOOM, NETHERLANDS Signed and Sealed this
Twenty-fourth Day of May, 2011

David J. Kappos
*Director of the United States Patent and Trademark Office*